(12) United States Patent
Clark (10) Patent No.: US 10,524,804 B2
(45) Date of Patent: Jan. 7, 2020

(54) HAND-HELD SPRING TOOL

(71) Applicant: Stryker Tools LLC, Airway Heights, WA (US)

(72) Inventor: Emory Clark, Airway Heights, WA (US)

(73) Assignee: Stryker Tools, LLC., Airway Heights, WA (US)

( * ) Notice: Subject to any disclaimer, the term of this patent is extended or adjusted under 35 U.S.C. 154(b) by 325 days.

(21) Appl. No.: 15/480,788

(22) Filed: Apr. 6, 2017

(65) Prior Publication Data

US 2018/0289377 A1 Oct. 11, 2018

(51) Int. Cl.
*A61B 17/16* (2006.01)
*A61B 17/92* (2006.01)

(52) U.S. Cl.
CPC .......... *A61B 17/1604* (2013.01); *A61B 17/92* (2013.01); *A61B 2017/925* (2013.01); *A61B 2017/928* (2013.01)

(58) Field of Classification Search
CPC .............. A61B 17/92; A61B 2017/925; A61B 2017/928; A61B 17/1604
USPC ............................................. 606/100; 30/367
See application file for complete search history.

(56) References Cited

U.S. PATENT DOCUMENTS

| 833,712 | A | * | 10/1906 | Geisenhoner | B25D 5/00 30/367 |
|---|---|---|---|---|---|
| 1,458,961 | A | * | 6/1923 | Williams | B25D 3/00 173/132 |
| 2,675,079 | A | * | 4/1954 | Hughes | C14B 5/00 30/367 |
| 3,172,204 | A | * | 3/1965 | Frey | B25D 5/02 30/367 |
| 4,682,412 | A | * | 7/1987 | Pfeffer | B25D 5/00 173/205 |
| 5,307,741 | A | * | 5/1994 | Clark | B44B 11/04 101/3.1 |
| D354,663 | S | * | 1/1995 | Clark | D8/14 |
| 5,426,858 | A | * | 6/1995 | Clark | B25D 5/00 30/358 |
| 5,433,007 | A | * | 7/1995 | Clark | B25C 3/006 30/360 |
| 5,662,686 | A | * | 9/1997 | Newsum | A61H 23/06 30/367 |
| 5,735,855 | A | * | 4/1998 | Bradley | A61B 17/151 606/79 |

(Continued)

*Primary Examiner* — David W Bates
(74) *Attorney, Agent, or Firm* — Wells St. John P.S.

(57) ABSTRACT

A hand-held spring-driven impact device (e.g., spring tool) configured with removable and replaceable tips. The spring tool may include a helical spring that is coupled to a first anvil at one end and a second anvil at the other end. The spring tool may include a locking mechanism on the first anvil and/or the second anvil. The locking mechanism may be configured to securely fasten a tip to the spring tool. The tip may include a single-sided tip or a double-sided tip. The spring tool may include an ergonomically curved gripping surface and/or a friction component to assist in holding the spring tool. In some examples, the spring tool may include a ball bearing situated between the first anvil and the second anvil to transfer impact force when applied at an angle. Additionally, the spring tool may include a cover to protect the spring during use.

8 Claims, 10 Drawing Sheets

(56) References Cited

U.S. PATENT DOCUMENTS

| | | | | |
|---|---|---|---|---|
| 6,010,508 | A * | 1/2000 | Bradley | A61B 17/151 |
| | | | | 606/86 R |
| 6,223,441 | B1 * | 5/2001 | Parsons | A62B 3/005 |
| | | | | 30/366 |
| 9,254,159 | B2 * | 2/2016 | Li | A61B 17/8866 |
| 2010/0331851 | A1 * | 12/2010 | Huene | A61B 17/92 |
| | | | | 606/100 |
| 2018/0010308 | A1 * | 1/2018 | Mandal | E01F 9/627 |

* cited by examiner

HAND-HELD SPRING TOOL

BACKGROUND

Hand-held spring-driven impact tools have been used for years in various different trades, such as construction, arts and crafts, and woodworking, to name a few (see e.g., U.S. Pat. No. 833,712 to Geisenhoener). Though the spring-driven impact tools are hand-held devices, the amount of force imparted on a tip of the tool may be substantial. Due to the substantial force imparted on the tip, conventional hand-held spring-driven impact tools include a tip that is forged with (or affixed to) an anvil as a single piece. However, the forged tips limit the use of a single apparatus based on the shape of the tip.

SUMMARY

This disclosure is directed to improved hand-held spring-driven impact tools (e.g., spring tools). In some examples, the spring tools may include removable and replaceable tips. The tips may be inserted and removed into a chamber of the spring tool, and may be securely held in place via a locking mechanism. The spring tools may be configured to accept a single-sided and/or a double-sided tip. In various examples, the spring tools described herein may be configured to be disassembled, such as for cleaning, sterilization, or the like. In some examples, the spring tools described herein may include ergonomically shaped gripping surfaces. Additionally, in some examples, the spring tools described herein may include one or more ball bearings to permit activation of the spring tool at an angle from an axis of the spring tool.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

As discussed above, this disclosure is directed to an improved spring-driven impact device (e.g., spring tool). In some examples, the improved spring tool may include a single-sided spring tool (i.e., a spring tool configured to accept a tip at one end) or a double-sided spring tool (i.e., a spring tool configured to accept a tip at both end). The spring tool may include a helical spring that is coupled to a first anvil (e.g., a plunger) at one end and a second anvil at the other end. In some examples, the spring tool may include removable and replaceable tips. In such examples, the spring tool may include a locking mechanism coupled to and/or situated at an end of the first anvil and/or the second anvil. The locking mechanism may be configured to securely fasten a tip to the spring tool.

In various examples, the locking mechanism may include a spring-loaded locking mechanism. In some examples, the spring-loaded locking mechanism may activate one or more ball bearings, pins, or other fastening mechanisms that are configured to retract for loading a tip, and extend to lock the tip in place. For example, a spring of a spring-loaded locking mechanism may be compressed, retracting two locking pins to permit insertion of a tip. The spring of the spring-loaded locking mechanism may be released, causing the two locking pins to extend out of the locking mechanism and engage into a groove of the tip. The tip may thus be secured into place in the locking mechanism.

In various examples, the locking mechanism may include one or more cam paths configured to receive one or more pins on the tip. In some examples, the cam paths may include two portions, each oriented in a different direction to secure the pins in place. For example, the pins be inserted into the locking mechanism and may track along a first portion of the cam path that is oriented substantially parallel to a horizontal axis of the tool. The tip may then be twisted so that the pin tracks along a second portion of the cam path configured substantially perpendicular to the first portion. For another example, the tip may be twisted so that the pin tracks along a second portion of the cam path configured at an angle between 90 degrees and 135 degrees from the first portion.

In various examples, the spring tool may be configured to securely house a single-sided and/or dual-sided tip. The tips may comprise screw drivers (e.g., cross-recess (i.e., Phillips®) head, blade-type (i.e., regular) head, hex key, Torx® head, etc.), pin punches, letter/number punches, shaped punches (e.g., cookie-cutter style punches), medical and/or dental device tips (e.g., bone chisels, bone gouges, bone osteotomes, etc.), multi-prong spears (e.g., knife edges), or the like.

The spring tool may include a gripping surface on each anvil. In various examples, the gripping surface may include a curved surface. In such examples, the curved surface may include an ergonomic curve designed for placement of a finger and/or thumb. In some examples, the gripping surface may include a substantially cylindrical surface. The gripping surface may be made of rubber, plastic, metal, or other non-slip material. Additionally, the gripping surface may include a traction feature to increase friction of the gripping surface. The traction feature may include knurls, pits, grooves, notches, raised surfaces (e.g., knobs, protrusions, nodes, etc.), anti-slip tape, and/or other features to increase the friction of the gripping surface. For example, the gripping surface may comprise a pitted rubber coating coupled to and surrounding the anvil.

In various examples, the spring tool may include one or more ball bearings situated between the first anvil and the second anvil. In such examples, upon release of an anvil, the impact force may transfer through the one or more ball bearings to the other anvil and consequently to the tip. The ball bearing(s) may be configured to permit an angled impact of the anvils.

In various examples, the spring tool may include a cover configured to substantially enclose the spring. In some examples, the cover may extend from a base of a first gripping surface to a base of a second gripping surface. In some examples, the cover may comprise a length substantially equivalent to the spring in a neutral (i.e., rest) position. In other examples, the cover may be longer or shorter in length than the spring.

In various examples, the spring tool may be configured to be disassembled. In such examples, the first anvil and/or the second anvil may be coupled to a respective end of the spring via a screw-type coupling. For example, a single sided spring tool (i.e., a spring tool configured to accept a tip at one end) may have a first anvil fixed to the spring at a first end, and a second anvil removably attached to the spring at a second end.

The apparatuses and techniques described herein may be implemented in a number of ways. Example implementations are provided below with reference to the following figures.

Figure 1:
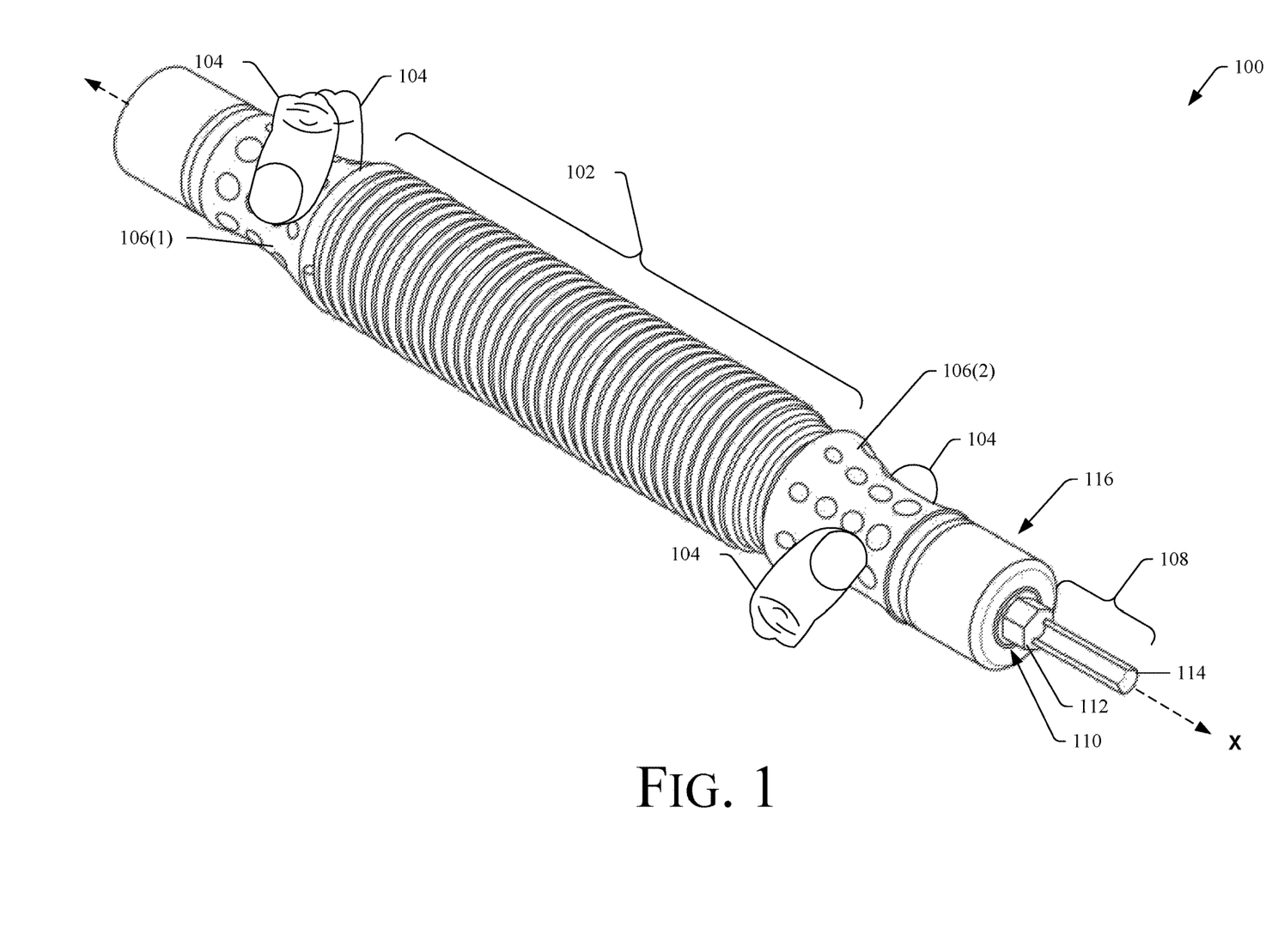
FIG. 1 is a perspective view of an example spring-driven impact device.

FIG. 1 is a perspective view of an example spring-driven impact device 100 (e.g., spring tool 100). The spring tool 100 may include a helical spring 102 coupled to a first anvil (not shown) (e.g., plunger) at one end and a second anvil (not shown) at the other end. The first and the second anvils may comprise a metal material (e.g., aluminum, steel, stainless steel, titanium, iron, alloys thereof, etc.), a plastic material (e.g., high-density polyethylene, acrylic, melamine, polycarbonate, etc.), a ceramic material, a graphite material, or another substantially rigid material.

The spring tool 100 may be operated by placing two or more fingers 104 on a gripping surface 106, and pulling (e.g., applying a force) substantially along an axis (X) of the spring tool 100. In the illustrative example, the gripping surfaces 106 may include a curved, concave shape configured for an ergonomic fit of one or more fingers 104. In some examples, the gripping surfaces 106 may include a curved, convex shape. In some examples, the gripping surfaces 106 may include a substantially flat surface around the spring tool (e.g., cylindrical shape of the gripping surface 106).

In various examples, the gripping surfaces 106 may include a portion of the first and the second anvils. In such examples, the portion of the first and the second anvils may be configured to accept one or more fingers 104 (e.g., configured so that one or more fingers can rest in the portion). In some examples, the gripping surfaces 106 may comprise a gripping component coupled to the portion of the first and the second anvils. In such examples, the gripping component may comprise a rubber material, a plastic material, or other non-slip material. Additionally, the gripping surfaces 106 may include a traction feature to increase friction of the gripping surface 106. The traction feature may include knurls, pits, grooves, notches, raised surfaces (e.g., knobs, protrusions, nodes, etc.), anti-slip tape, and/or other features to increase the friction of the gripping surface 106. For example, the gripping surface 106 may comprise a pitted rubber coating surrounding a portion of the first anvil and the second anvil.

Applying a force (e.g., pulling) along the X-axis may cause the spring to extend from a neutral (i.e., rest) position depicted in FIG. 1. In an extended position, the first anvil and the second anvil may be separated. The fingers 104 holding gripping surface 106(1) may release, causing the spring to retract toward the neutral position. In the neutral position, the first anvil (e.g., anvil comprising the gripping surface 106(1)) may strike the second anvil, transferring kinetic energy from the first anvil to the second anvil. The kinetic energy may transfer through the second anvil to a tip 108 coupled thereto.

The tip 108 may comprise a screw driver (e.g., cross-recess (i.e., Phillips®) head, blade-type (i.e., regular) head, hex key, Torx® head, etc.), a pin punch, a letter/number punch, a shaped punch (e.g., cookie-cutter style punches), a medical and/or dental device tip (e.g., bone chisels, bone gouges, bone osteotomes, etc.), a multi-prong spear (e.g., multiple knife edges, multiple shafts with pointed tips), a single-prong spear (e.g., a single knife edge, single shaft with a pointed tip), a tent stake, or the like. The tip may comprise a base section configured to fit within a chamber 110 of the spring tool 100. In the illustrative example, the chamber 110 and the base section 112 comprise a hexagonal shape. In other examples, the chamber 110 and the base section 112 may comprise an octagonal shape, a rectangular shape, a triangular shape, a cylindrical shape, or another shape.

As will be discussed in greater detail below, the tip 108 may include one end section 114 or two end sections 114. In other words, the tip 108 may be single or double-sided. In examples with a single-sided tip 108, the end portion 114 may protrude outward from the chamber 110 (e.g., from an end of the spring tool 100). For example, the tip 108 depicted in FIG. 1 includes a base section 112 inserted into the chamber 110, with an end section 114 comprising a U-shaped chisel. In examples with a double-sided tip 108, a second end section 114 may be inserted into a housing extending inward from the chamber 110 (e.g., toward a center of the device). For example, the tip 108 may include a first end section 114 coupled to a first end of the base section 112 and configured to protrude outward from the chamber 110 and a second end section 114 coupled to a second end of the base section 112, the second end section extending inward from the chamber 110 and being stored in the housing.

In various examples, the tip 108 may comprise part of the first or the second anvil, such as in a single molded element. In some examples, the tip 108 may be removable and replaceable. In such examples, the tip 108 may be inserted into and removed from the chamber 110 of the spring tool 100. In various examples, the tip 108 may be locked into place in the chamber 110, such as via a locking mechanism 116.

In various examples, the locking mechanism 116 may include a spring-loaded locking mechanism 116. The spring-loaded locking mechanism 116 may be coupled to the first and/or the second anvil, at an end of the spring tool 100. As will be discussed in greater detail with regard to FIG. 3, the spring-loaded locking mechanism 116 may activate one or more ball bearings, locking pins, or other fastening mechanisms that are configured to retract for loading a tip 108, and extend to lock the tip 108 in place. For example, a spring of a spring-loaded locking mechanism may be compressed, retracting two ball bearings to permit insertion of a tip 108. The spring of the spring-loaded locking mechanism may be released, causing the two ball bearings to extend out of the locking mechanism and engage into a groove of the tip. The tip 108 may thus be secured into place in the locking mechanism 116.

In various examples, the locking mechanism 116 may include one or more cam paths configured to receive one or more locking pins on the tip 108. In such examples, the cam paths may comprise cutouts inside the chamber 110. In some examples, the cam paths may include two portions, each oriented in a different direction to secure the pin in place. For example, the pin be inserted into the locking mechanism 116 and may track along a first portion of the cam path that is oriented substantially parallel to the X-axis of the tool. The tip may then be twisted to track along a second portion of the cam path configured substantially perpendicular to the first portion (i.e. the X-axis). For another example, the tip may be twisted to track along a second portion of the cam path configured at an angle between 90 degrees and 135 degrees from the first portion.

Figure 2:
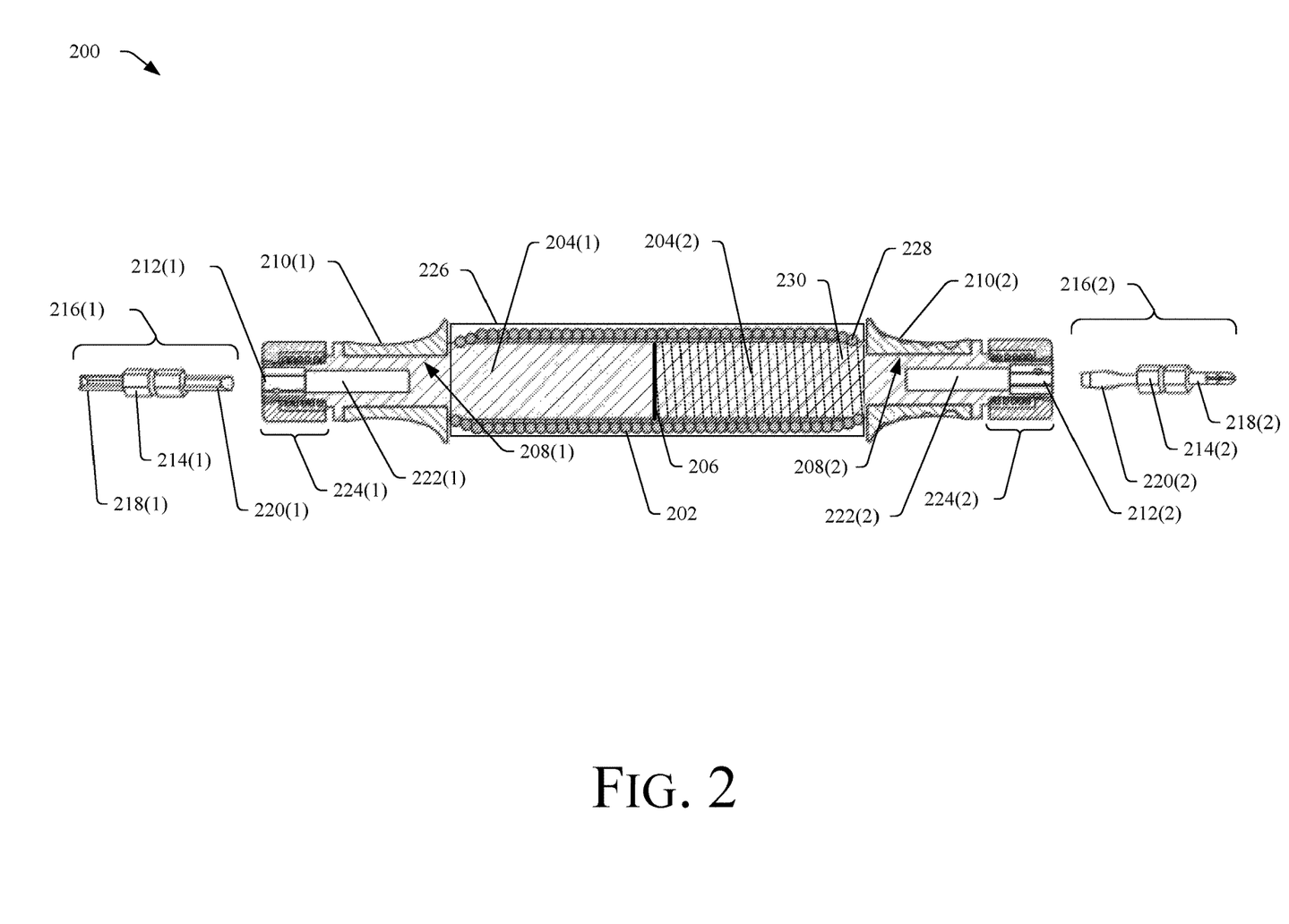
FIG. 2 is a side cross-sectional view of an example spring-driven impact device.

FIG. 2 is a side cross-sectional view of an example spring-driven impact device (e.g., spring tool) 200, such as spring tool 100. The spring tool 200 may comprise a spring 202 (i.e., helical or coil spring) coupled at a first end to a first anvil 204(1) and at a second end to a second anvil 204(2). In some examples, the first anvil 204(1) and the second anvil 204(2) may be configured to rest adjacent to one another at a striking point 206, when the spring is in a retracted position. The striking point 206 may include the point at which kinetic energy from a moving anvil may transfer to the other anvil and a tip coupled to the other anvil, such as described above in the discussion of FIG. 1.

In various examples, the first anvil 204(1) and the second anvil 204(2) may be configured to rest adjacent to one or more bearings when the spring is in a retracted position. In such examples, the ball bearing(s) may transfer kinetic energy from the moving anvil to the other anvil and consequently to the tip coupled thereto.

In the illustrative example, the anvils 204 may comprise a cutout 208 configured to house a gripping surface 210. The cutout 208 may extend a length of an outer surface around a circumference of the spring tool 200. In some examples, the gripping surface 210 may comprise a rubber material, a plastic material, or other non-slip material. In other examples, the gripping surface 210 may comprise a portion of the anvils 204. In such examples, the gripping surface 210 and the anvil 204 may comprise a single molded piece.

As illustrated in FIG. 2, the gripping surface 210 may include a curved surface. In such examples, the curved surface may be configured for an ergonomic fit of one or more fingers, such as gripping when the spring tool 100 at the gripping surfaces 210(1) and 210(2). In some examples, the gripping surface 210 may include a substantially flat surface, such as in a substantially cylindrical shape.

In various examples, the gripping surface 210 may include a traction feature to increase friction of the gripping surface. The traction feature may include knurls, pits, grooves, notches, raised surfaces (e.g., knobs, protrusions, nodes, etc.), anti-slip tape, and/or other features to increase the friction of the gripping surface 210. In some examples, a first gripping surface 210(1) may include a traction feature and the second gripping surface 210(2) may include a smooth surface. In some examples, a first gripping surface 210(1) may include a first traction feature and the second gripping surface 210(2) may include a second traction feature. For example, the first gripping surface 210(1) may comprise multiple raised surfaces and the second gripping surface 210(2) may comprise pitted rubber coating.

The spring tool 200 may include a chamber 212 at an outer end of the anvil 204. The chamber 212 may be configured to house a base section 214 of a tip 216. The chamber 212 and the base section 214 may comprise substantially the same shape, such as a cylindrical shape, a triangular shape, a rectangular shape, a hexagonal shape, an octagonal shape, or another shape.

In some examples, the tip 216 may comprise the base section 214 and a first end section 218. In such examples, the tip 216 may be a single-ended tip. In some examples, the tip 216 may comprise the base section, the first end section 218, and a second end section 220. In such examples, the tip 216 may comprise a double-ended tip. In various examples, the anvil may comprise a housing 222 extending inward from the chamber 212. The housing 222 may be configured to house the second end section 220, when the first end section 218 is in use, or vice versa.

In various examples, the tip 216 may be securely fastened within the chamber 212 and/or the housing 222 via a locking mechanism 224. In some examples, the locking mechanism 224 may comprise a spring-driven locking mechanism, such as the example described below with regard to FIG. 3. In some examples, the locking mechanism 224 may comprise a cam path locking mechanism, such as the example described below with regard to FIG. 4.

In various examples, the spring tool 200 may additionally include a cover 226 extending over the spring 202. The cover 226 may comprise a metal material, a plastic material, or other substantially rigid material. In various examples, the cover 226 may include a length substantially equivalent to a length of the spring 202 in the neutral (i.e., rest) position. In some examples, the cover 226 may include a length greater or less than the length of the spring 202 in the neutral position. In some examples, the cover 226 may be configured to be removed from the spring tool 200.

As discussed above, the spring 202 may be coupled at a first end to a first anvil 204(1) and at a second end to a second anvil 204(2). In various examples, the spring 202 at either end may decrease in diameter. In such examples, two or more rungs 228 at the end of the spring 202 may be coiled more tightly, thereby decreasing in diameter. In various examples, the two or more rungs 228 may seat into a cutout into the anvils 204 inward of the cutout 208 and/or the gripping surface 210. In such examples, the spring 202 may be securely coupled to the anvils 204. In some examples, the anvils 204 may comprise grooves 230 (e.g., screw-type grooves). The grooves 230 may comprise indentations into a surface of the anvil 204, extending around a circumference of the anvil 204. The rung(s) 228 may be configured to track along each groove 230. In various examples, the grooves 230 may facilitate the separation of various components of the spring tool 200. For example, each anvil 204(1) and 204(2) may be screwed into respective ends of the spring via the rungs 228 tracking along the grooves 230, to build the spring tool 200, and may be unscrewed to disassemble the tool, such as for cleaning, sterilizing, etc.

Figure 3:
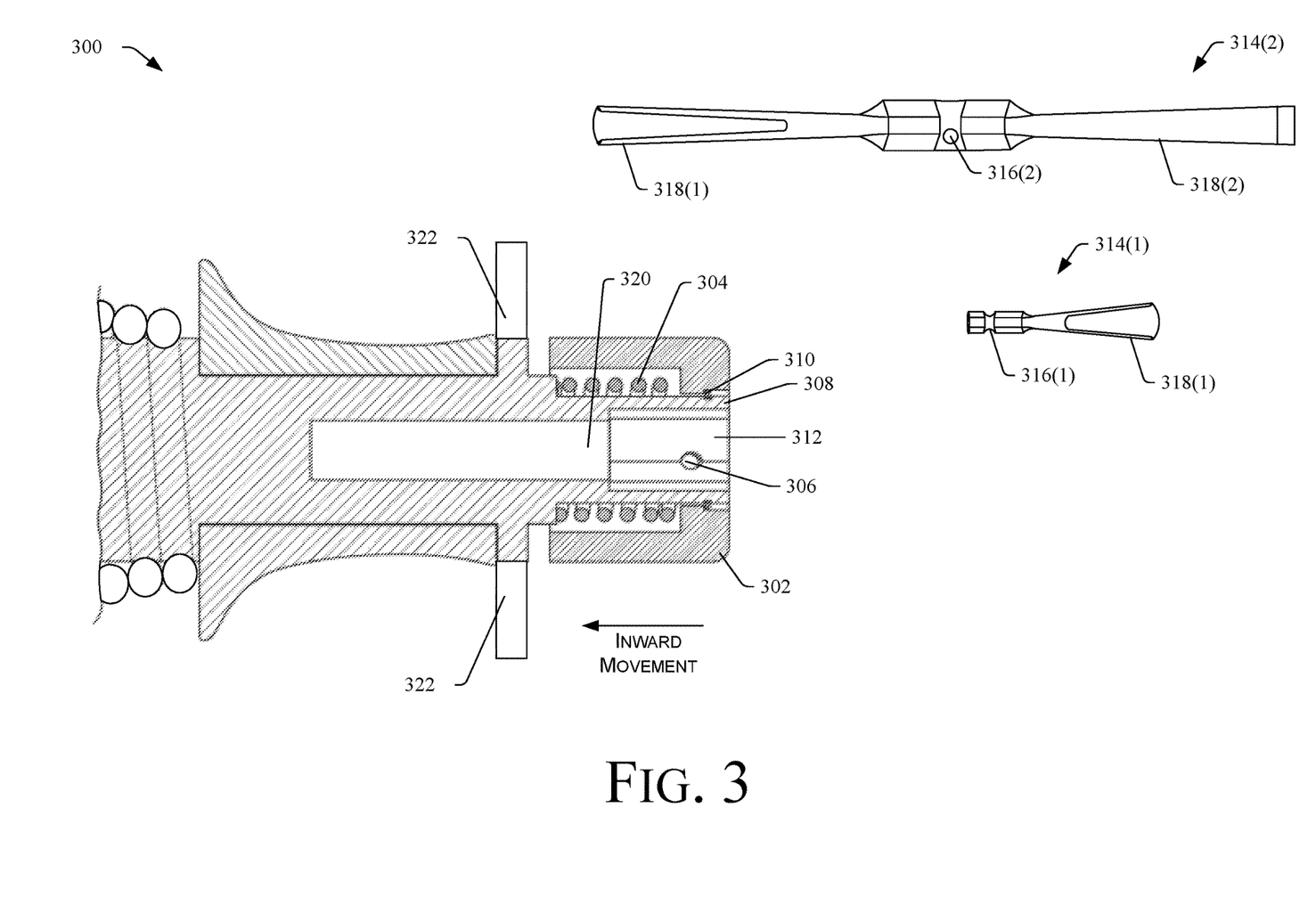
FIG. 3 is a side cross-sectional view of an example locking mechanism of a spring-driven impact device.

FIG. 3 is a side cross-sectional view of an example locking mechanism 300 of a spring-driven impact device. The locking mechanism 300 comprises a spring-driven locking mechanism. The locking mechanism 300 may include a cap 302, a spring 304, and one or more fastening mechanisms 306 (e.g., locking ball, locking pin, etc.). In various examples, the locking mechanism 300 may be mounted to an end of an anvil 308, such as anvil 204.

As illustrated in FIG. 3, the locking mechanism 300 may be held in place by a protruding member 310 of the anvil. The protruding member 310 may permit inward movement of the cap (e.g., toward a center of the device as shown by the arrow). The inward movement of the cap may cause the spring 304 to compress from a neutral (i.e., rest) position as depicted in FIG. 3, to a compressed position. A compression of the spring 304 may cause the fastening mechanism(s) 306 to retract out of a chamber 312 configured to house a tip 314. With the fastening mechanism(s) 306 in a retracted position, the tip 314 may be inserted. Once inserted, the cap 302 may be released, causing the spring to extend toward the neutral position and the fastening mechanism 306 to extend into the chamber 312. In an extended position, the fastening mechanism may be seated in a groove 316 of the tip 314. In some examples, the groove 316 may extend around a body of the tip, such as groove 316(1). In some examples, the groove 316 may comprise an indentation in the base portion that is configured to receive the fastening mechanism, such as groove 316(2).

In various examples, the tip 314 may be single-sided, such as tip 314(1). In such examples, the tip 314(1) may include a first end section 318(1). In the illustrative example, the first end section 318(1) comprises a gouge, such as that used for medical and/or dental work. In other examples, the first end section 318(1) may comprise any other type of tip, such as, for example, a screwdriver head, another medical and/or dental device head, a craft punch, etc., based on a current use of the spring tool. For example, in a first use, the spring tool may be used to unfasten a screw. A user may insert a tip 314 with a screwdriver end section 318 into the chamber 312. The user may place the screwdriver end section 318 in a top end of the screw. The user may pull a second anvil away from the tip 314 with the screwdriver end section 318, and may release the second anvil, causing the screwdriver end section 318 to loosen the screw. The user may then twist the spring tool with the screwdriver end section 318 engaged in the top end of the screw to unfasten the screw. After unfastening the screw, the user may then remove the tip 314 with the screwdriver end section 318, and insert a tip 314 with a chisel end section 318.

In various examples, the spring tool 300 may include to two extending members 322, situated on opposite sides of an anvil. The extending members 322 may assist a user in applying torque at the end of the spring tool (i.e., at the tip). Using the screwdriver example above, a user may loosen the screw, and hold the extending members 322 while twisting the spring tool with the screwdriver end section 318 engaged in the top end of the screw. The user may thus be able to generate an increased amount of torque on the screwdriver end section 318. In some examples, the extending member 322 may comprise a portion of the anvil. In such examples, the anvil may be molded or forged with the extending members 322. In some examples, the extending members 322 may separate components of the spring tool. In various examples, the extending members 322 may be removable and replaceable. For example, the extending members 322 may be configured to slide into a groove cutout into the anvil, on opposite sides of the anvil.

In various examples, the tip 314 may be double-sided, such as tip 314(2). In such examples, the tip 314(1) may include a first end section 318(1) and a second end section 318(2). In the illustrative example, the first end section 318(1) comprises a gouge and the second end section 318(2) comprises a chisel. However, as mentioned above, in other examples, the first end section 318(1) and the second end section 318(2) may comprise another type of tip based on a use of the spring tool. In examples with a double-sided tip 314(2), the spring tool may be configured with a housing 320. The housing 320 may be configured to house the end section 318 not in use. For example, a user may currently be use the chisel end section 318(2), but may want to switch to using the gouge end section 318(1). The user may release the locking mechanism 300 to remove the tip 314(2), and may reinsert the tip 314(2) with the gouge end section 318(1) protruding from the chamber 312.

Figure 4:
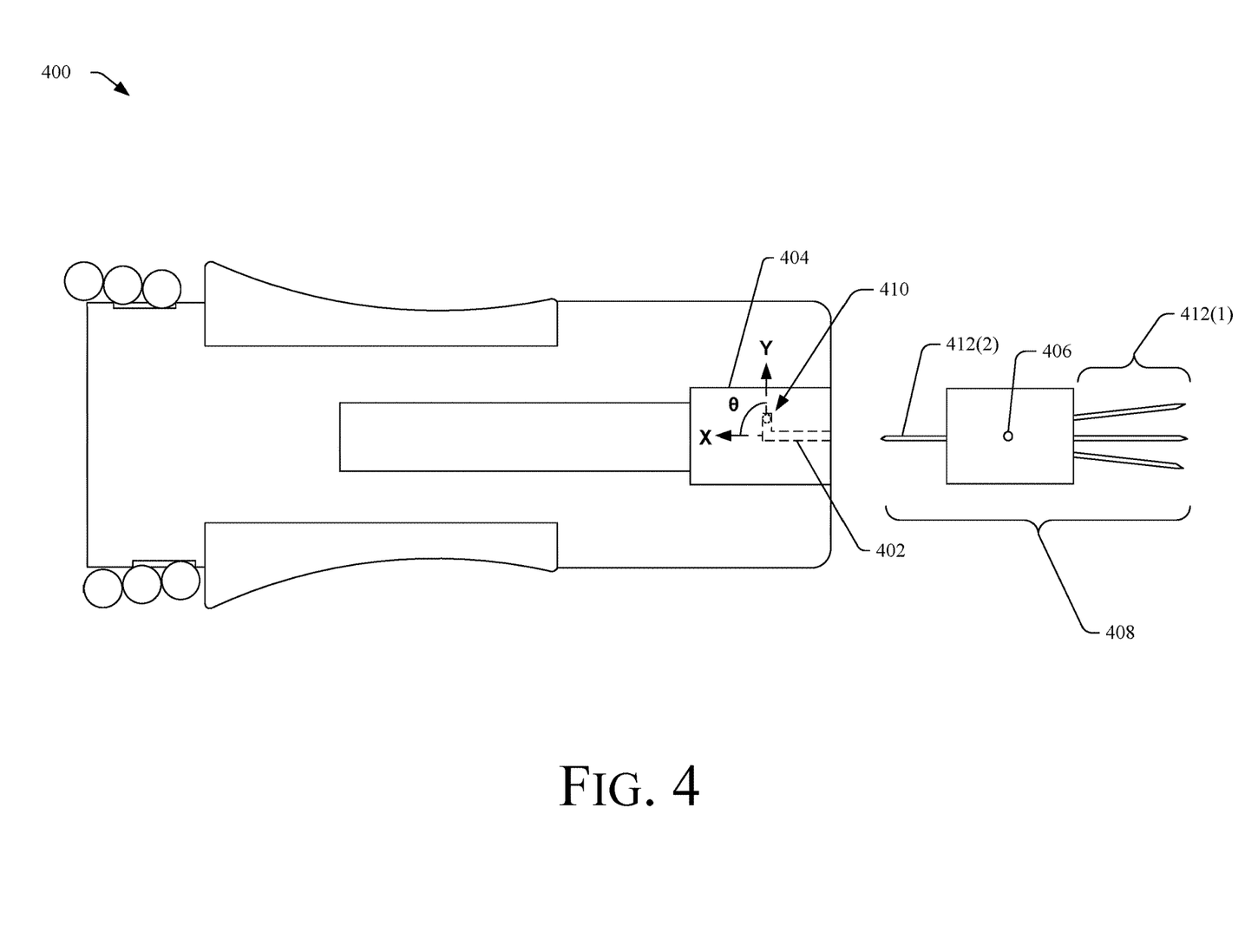
FIG. 4 is a side cross-sectional view of another example locking mechanism of a spring-driven impact device.

FIG. 4 is a side cross-sectional view of another example locking mechanism 400 of a spring-driven impact device. The locking mechanism 400 may include one or more cam paths 402 in a chamber 404, and one or more locking pins 406 on a tip 408. The cam path(s) 402 may comprise cutouts inside the chamber 404. In the illustrative example, the cam path 402 comprises a first portion oriented along an X-axis of the spring tool, and a second portion oriented substantially perpendicular, along a Y-axis. In such examples, the cam path 402 may be L-shaped. In some examples, an angle θ may include an angle between 90-135 degrees. In various examples, the locking mechanism 400 may include a third portion oriented substantially parallel with the first portion, such that the cam path 402 is substantially U-shaped.

In various examples, the cam path(s) may be configured to receive the locking pin(s) on the tip 408. The locking pin 406 may track along the cam path 402, and may secure into place at a locked position 410. The tip 408 may be secure in the locked position 410 during use of the spring tool, and may be easily removed by tracking the pin 406 along the cam path and out of the chamber. For example, the tip 408 may include a fishing apparatus, with a first end section 412(1) comprising a multi-prong spear, and a second end section 412(2) comprising a fileting knife. A user may first use the multi-prong spear on the first end section 412(1) to humanely kill a fish, such as by piercing the brain with the multi-prong spear. After killing the fish with the first end section 412(1), the user may remove the tip 408 from the chamber 404, and reinsert the tip 408 with the second end section 412(2) protruding from the chamber, to filet the fish.

Figure 5:
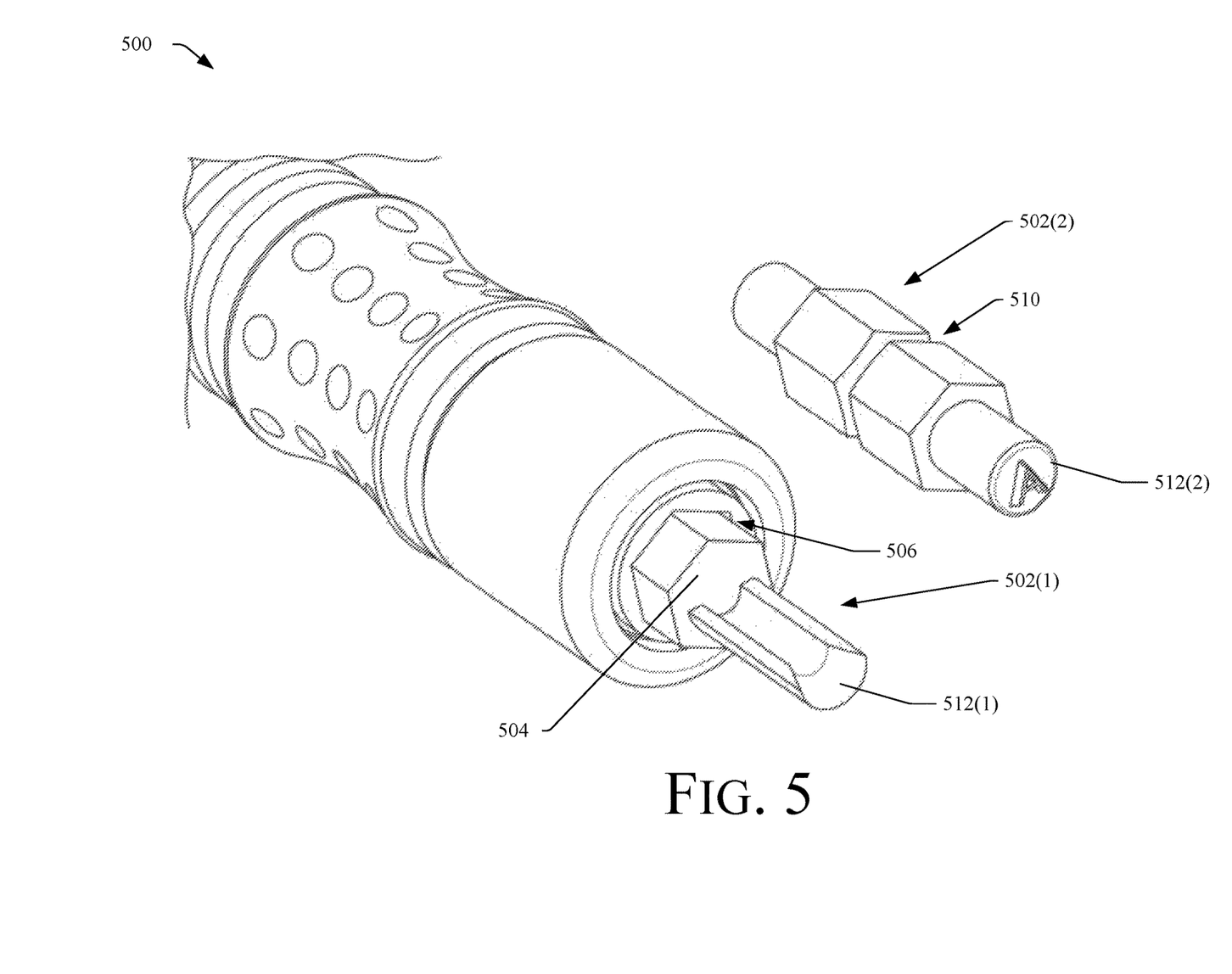
FIG. 5 is a perspective view of an end of a spring-driven impact device with a tip inserted.

FIG. 5 is a perspective view of an end of a spring-driven impact device (e.g., spring tool) 500, such as spring tool 100, 200, with a tip 502, such as tip 108, 216, 314, and 408, inserted. As discussed above, a base section 504 of the tip 502 may be inserted into a chamber 506, such as chamber 110, 212, 312,404, of the spring tool 500. In the illustrative example, the chamber 504 and the base section 504 comprise a hexagonal shape. In other examples, the chamber 504 and the base section 504 may comprise a cylindrical shape, a triangular shape, a rectangular shape, an octagonal shape, or other shape. As discussed above with regard to FIG. 3, the tip 502 may be securely fastened into the chamber 506 by a fastening mechanism being set into a groove 510 of the tip 502.

The fastening mechanism may securely hold the tip 502 in place, but may permit an easy release of the tip, such as to remove tip 502(1) with tip 502(2). For example, while woodworking, a user may use a U-shaped end section, such as end section 512(1). The user may then want to stamp letters into the wood. The user may replace the tip 502(1) with the tip 502(2) comprising a letter punch end section, such as end section 512(2).

Figure 6:
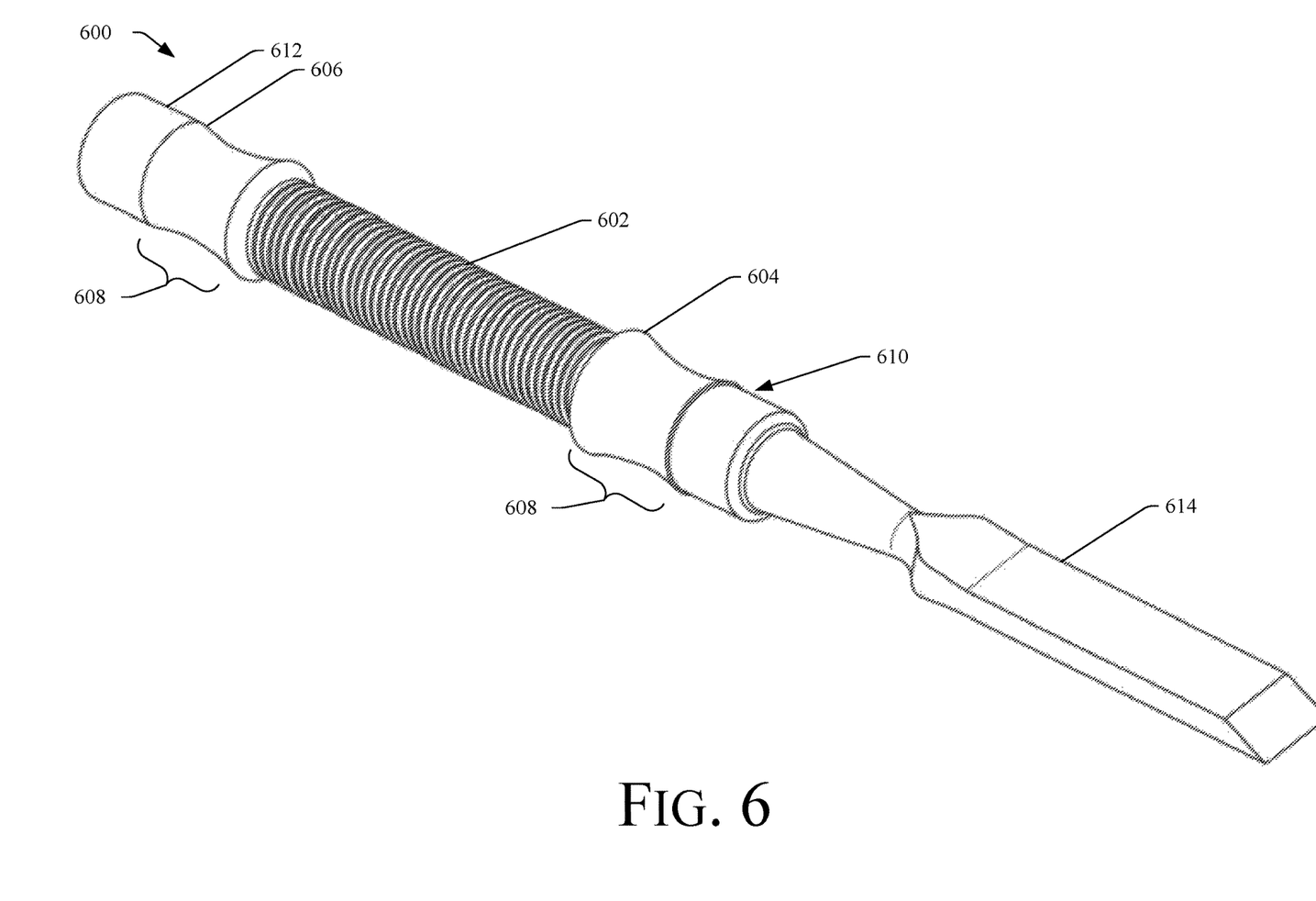
FIG. 6 is a perspective view of an example single-sided spring-driven impact device.

FIG. 6 is a perspective view of an example single-sided spring-driven impact device 600 (e.g. spring tool 600). The spring tool 600 may include a helical spring 602 coupled to a first anvil 604 at one end and a second anvil 606 at the other end. The first anvil 604 and the second anvil 606 may comprise a metal material (e.g., aluminum, steel, stainless steel, titanium, iron, alloys thereof, etc.), a plastic material (e.g., high-density polyethylene, acrylic, melamine, polycarbonate, etc.), a ceramic material, a graphite material, or another substantially rigid material.

In various examples, the spring 602 may be coupled to the first anvil 604 and/or the second anvil 606 via a screw-type coupling. In such examples, the components of the spring tool 600 may be configured to be disassembled (e.g., the spring tool 600 may be taken apart), such as for cleaning, sterilization, etc. In some examples, the spring 602 may be coupled to the first anvil 604 and/or the second anvil 606 by decreasing the size of a coil of the spring 602 at each end, and engaging the smaller sized portion of the coil in a notch of the first anvil 604 and/or the second anvil 606. In such examples, the components of the spring tool 600 may not be configured to be disassembled.

The first anvil 604 and the second anvil 606 may comprise gripping surfaces 608, such as gripping surfaces 106, 210. The gripping surfaces 608 may comprise gripping portions of the anvils 604 and 606, configured to fit two or more fingers during use of the spring tool 600. In some examples, the gripping surfaces 608 may comprise the same material as the anvils 604 and 606. In some examples, the gripping surfaces 608 may comprise a different material. In such examples, the gripping surfaces 608 may comprise a non-slip material (e.g., rubber, plastic, non-slip tape, or the like) placed over the gripping portions.

In the illustrative example, the gripping surfaces 608 comprise a substantially cylindrical shape. In other examples, the gripping surfaces 608 may comprise a convex shape, a concave shape, a U-shape, or other shape configured to assist in holding one or more fingers on the gripping surface 608. Additionally, in the illustrative example, the gripping surfaces 608 comprise a smooth surface. In other examples, the gripping surfaces 608 may comprise a textured surface, such as a knurled surface, a pitted surface, a notched surface, or other texture and/or feature to increase friction of the gripping surfaces 608.

As mentioned above, the spring tool 600 may comprise a single-sided spring tool. In such an example, the spring tool 600 may include a single chamber 610 located at an outer end of an anvil 604 or 606 (illustrated as the first anvil 604). In the illustrative example, the spring tool 600 includes a cap 612 at an outer end of the other anvil (illustrated as anvil 606). In other examples, the cap 612 may comprise an outer portion of the other anvil.

As illustrated in FIG. 6, the spring tool 600 may include a tip 614, such as tip 108, 216, 314, 408, 502. In the illustrative example, the tip 614 comprises a chisel, such as that used in orthopedics or dental surgery. In other examples, the tip may comprise a gouge, osteotome, or other medical and/or dental device tip, a punch (e.g., a pin punch, a letter punch, a number punch, a shaped punch (e.g., cookie-cutter style punch, punch for carving jack o' lanterns, etc.), or the like), a spear, a knife, a screw driver, a woodworking chisel (e.g., a U-shaped chisel, a V-shaped chisel, etc.), a tent stake, or any other type of tip. The tip 614 may comprise a single sided tip, such as tip 314(1), or a double-sided tip, such as tip 314(2). In examples with a double-sided tip, the anvil 604 may be configured with a housing, to store an end section of the tip that is not protruding outward from the spring tool 600.

Figure 7A:
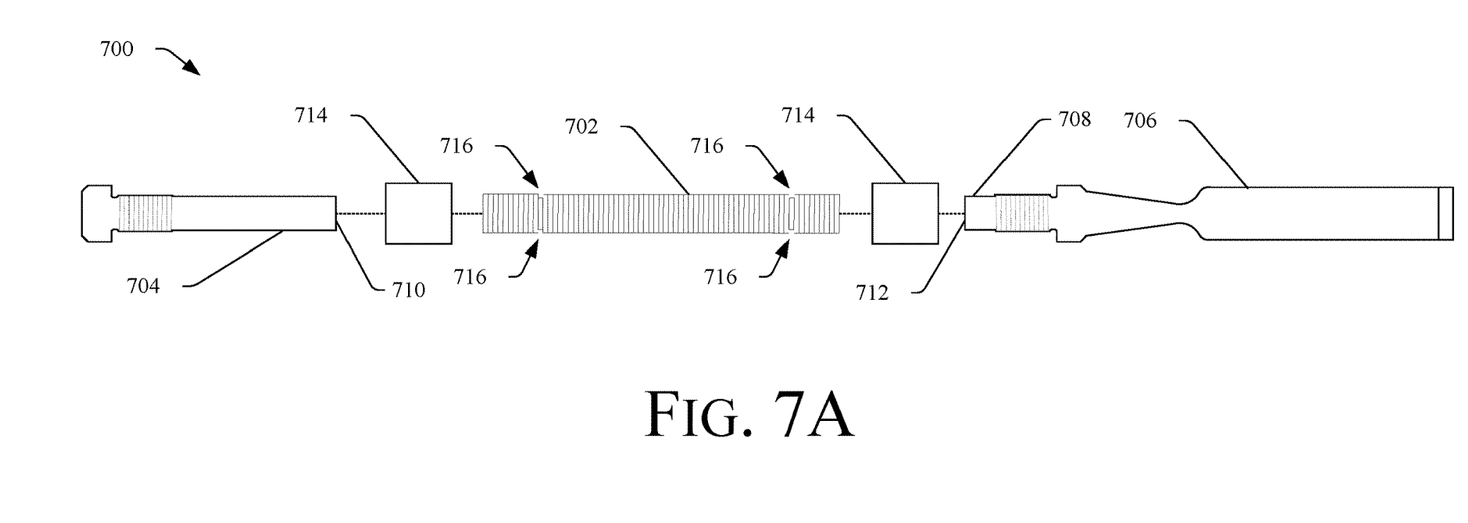
FIG. 7A is an exploded view of an example single-sided spring-driven impact device.

FIG. 7A is an exploded view of an example single-sided spring-driven impact device 700 (e.g., spring tool 700), such as spring tool 600. The spring tool 700 may be configured to be disassembled, such as for cleaning, sterilization, or the like.

In some examples, the spring tool 700 may include a spring 702, a first anvil 704 and a tip 706, such as such as tip 108, 216, 314, 408, 502, 614. In some examples, the tip 706 may be coupled to a second anvil 708 via a locking mechanism, such as locking mechanism 116, 400, etc. In the illustrative example, the second anvil 708 and the tip 706 may comprise a single molded material. In such examples, an inner surface 710 the first anvil 704 may be configured to be adjacent to an inner surface 712 of the tip 706 (and the second anvil 708) when the spring tool 700 is in a neutral (i.e., rest) position (such as that shown in FIG. 7B).

In various examples, the first anvil 704, the tip 706, and/or the second anvil 708 may be configured to couple to the spring 702. In the illustrative example, the coupling comprises a screw-type coupling. For example, the tip 706 and/or the second anvil 708 may comprise grooves, such as grooves 230, and may be configured to screw into an end of the spring. The first anvil 704 may also comprise grooves, and may be configured to screw into the other end of the spring. In other examples, the coupling may comprise a different type of mechanical coupling.

In some examples, the spring tool 700 may comprise spring end caps 714. In such examples, the spring end caps 714 may couple to respective ends of the spring 702. In some examples, the spring end caps 714 may couple to the spring 702 via one or more notches 716. The spring end caps 714 may act as a casing for the end of the spring 702, preventing the respective end of the spring 702 from expanding in diameter when the first anvil 704, tip 706 and/or the second anvil 708 is screwed thereto. Accordingly, the spring end caps 714 may assist in further securing the first anvil 704, and the second anvil 708 and/or the tip 706 to the spring.

Figure 7B:
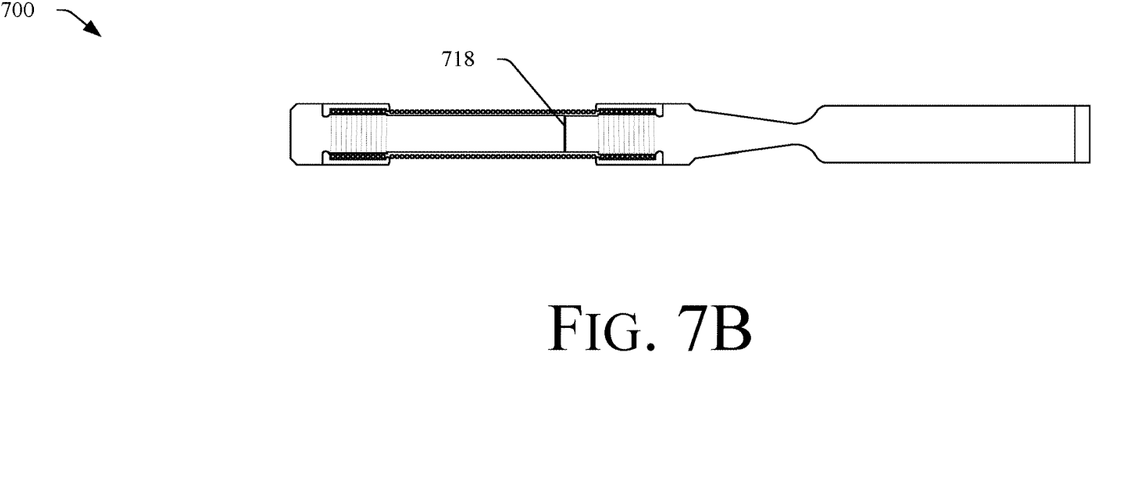
FIG. 7B is a side cross sectional view of the example spring-driven impact device described in FIG. 7A.

FIG. 7B is a side cross sectional view of the spring tool 700. As described above, the inner surface the first anvil 704 may be configured to be adjacent to the inner surface of the tip 706 (and the second anvil 708) at a striking point 718 when the spring tool 700 is in the neutral position. The striking point 718 comprises the point at which the first anvil 704 transfers kinetic energy to the tip 706 of the spring tool 700.

Figure 8A:
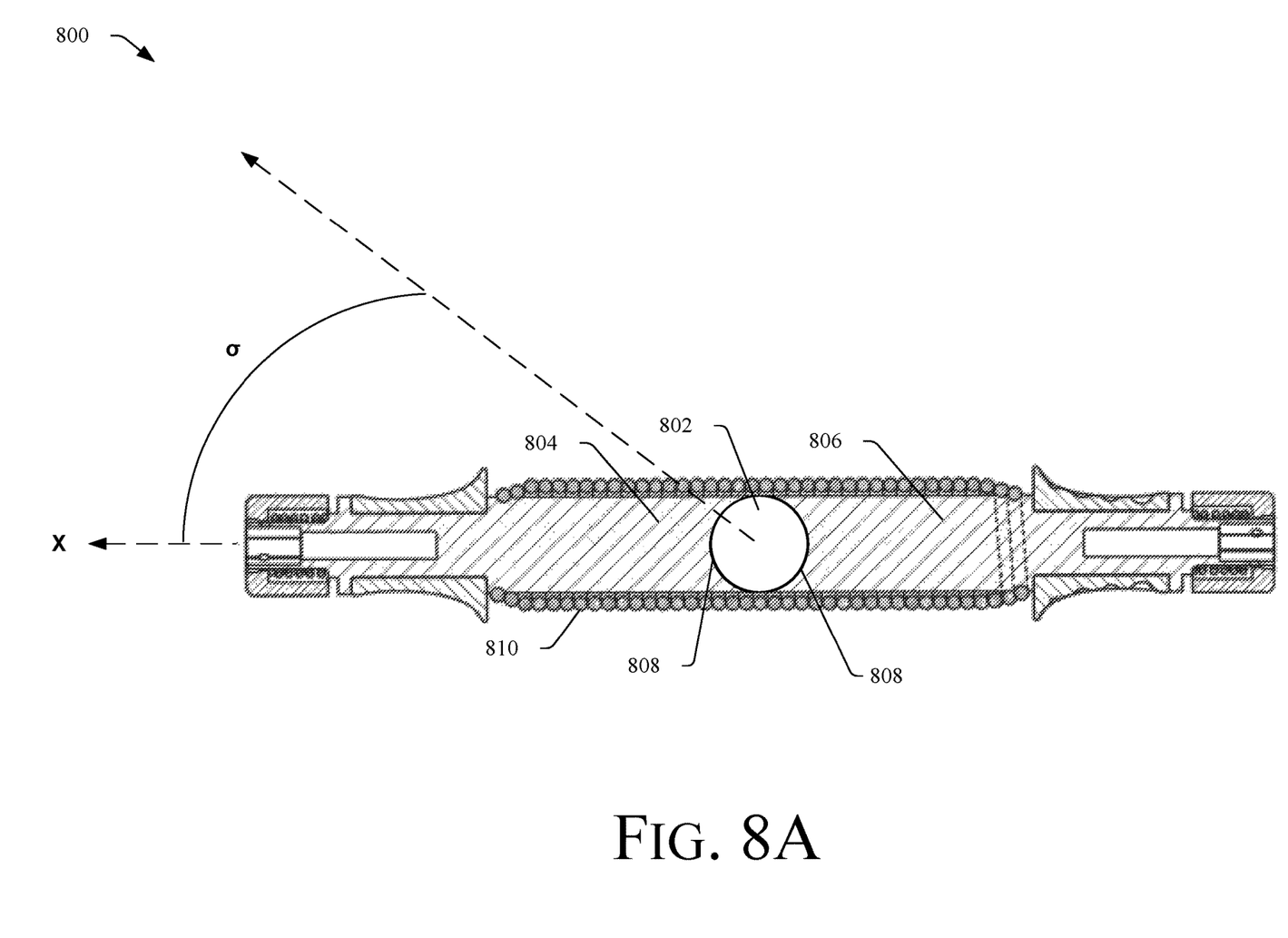
FIG. 8A is a side cross-sectional view of an example spring-driven impact device configured with a single ball bearing situated between anvils.

FIG. 8A is a side cross-sectional view of an example spring-driven impact device 800 (e.g., spring tool 800), such as spring tool 100, 200, 600, 700, configured with a single ball bearing 802 situated between a first anvil 804 and a second anvil 806. In various examples, the inner ends of the first anvil 804 and the second anvil 806 may be substantially shaped to conform to the round shape of the ball bearing 802. In such examples, the striking point 808 may include a substantial portion of the inner end of the anvil 804 and 806. In some examples, the inner ends of first anvil 804 and 806 may comprise a substantially flat surface. In such examples, the striking point may include a point at which the ball bearing 802 and the anvils 804 and 806 strike one another.

In various examples, the ball bearing 802 may be configured to transfer energy from a moving anvil (e.g., anvils 804 or 806) to a non-moving anvil (e.g., the other anvil 804 or 806). As will be discussed in further detail below with regard to FIG. 7B, the ball bearing 802 may permit a moving anvil to be pulled at an angle (σ) from the X-axis of the spring tool 800, without damaging the spring. In some example, the angle σ may include an angle of 90 degrees or less.

In some examples, the ball bearing 802 may be coupled to a spring 810 of the spring tool 800. In such examples, the ball bearing 802 may be fixed in place in the spring tool 800. In various examples, the ball bearing 802 may be configured to freely move inside the spring 810, responsive to one or both anvils moving. For example, during use of the spring tool, the first anvil 804 may be pulled away from the ball bearing 802 and the second anvil 806. Responsive to the first anvil 804 being moved away from the rest position adjacent to the ball bearing 802, the ball bearing 802 may be free to move (i.e., roll) interior to the spring, between the first anvil 804 and the second anvil 806. In various examples, inner portions of the first anvil 804, the second anvil 806, and the ball bearing 802 may be encased in a flex tube. In such examples, the ball bearing 802 may be configured to freely move inside the flex tube. The flex tube may comprise a material configured to flex and stretch, such as a plastic material, an elastic material, or a combination of the foregoing.

FIG. 7B is a side cross-sectional view of the spring-driven impact device 800 shown in FIG. 7A deviated at an angle from the X-axis. In conventional spring tool models, a deviation from the X-axis during use may cause damage to the spring. In some examples, the damage can render the spring tool unusable. To remedy this limitation of the conventional models, the ball bearing 802 may permit an anvil to be pulled at an angle σ from the X-axis, and used at the angle σ, without damaging the spring. In some example, the angle σ may include an angle of 135 degrees or less.

For example, the first anvil 804 may be pulled outward and rotated away from the X-axis at the angle σ. The first anvil 804 may then be released. Responsive to release, the spring 810 may contract, pulling the first anvil 804 back toward the ball bearing 802. The first anvil 804 may strike the ball bearing 802, which may transfer energy to the second anvil 806 and consequently a tip of the spring tool 800. The spring 810 may also cause the first anvil 804 to be reoriented along the X-axis in the rest position substantially at the same time, or just after the energy transfer.

Figure 9:
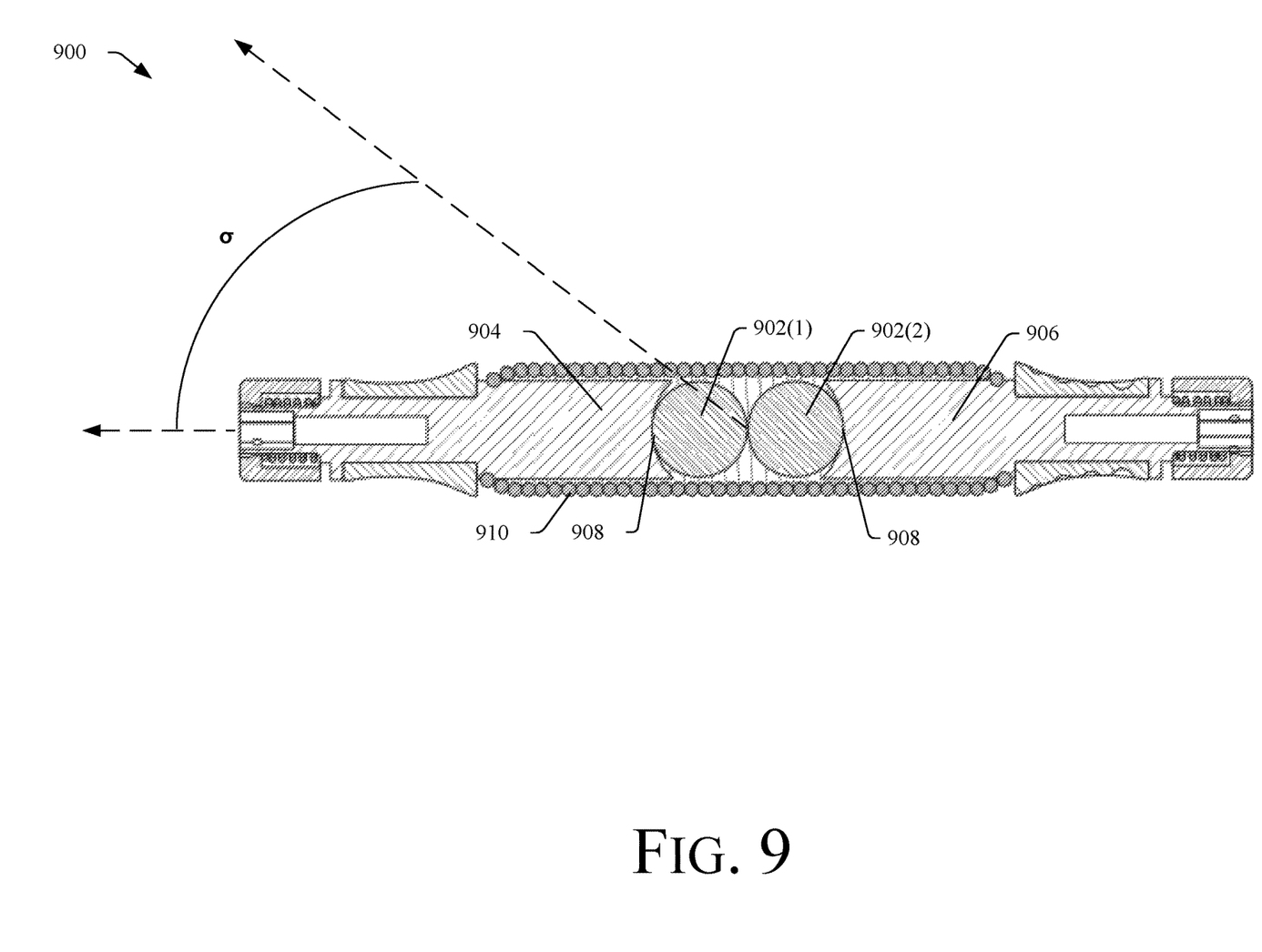
FIG. 9 is a side cross-sectional view of an example spring-driven impact device configured with two ball bearings situated between anvils.

FIG. 9 is a side cross-sectional view of an example spring-driven impact device 900 (e.g., spring tool 900), such as spring tool 100, 200, 600, 700, 800, configured with two ball bearings 902(1) and 902(2) situated between a first anvil 904 and a second anvil 906. In various examples, the inner ends of the first anvil 904 and the second anvil 906 may be substantially shaped to conform to the round shape of the first ball bearing 902(1) and the second ball bearing 902(2), respectively. In such examples, the striking points 808 may include a substantial portion of the inner end of the anvil 904 and 906. In some examples, the inner ends of first anvil 904 and the second anvil 906 may comprise a substantially flat surface. In such examples, the striking points may include a point at which the ball bearings 902(1) and 902(2), and the anvils 904 and 906, strike one another.

Figure 8B:
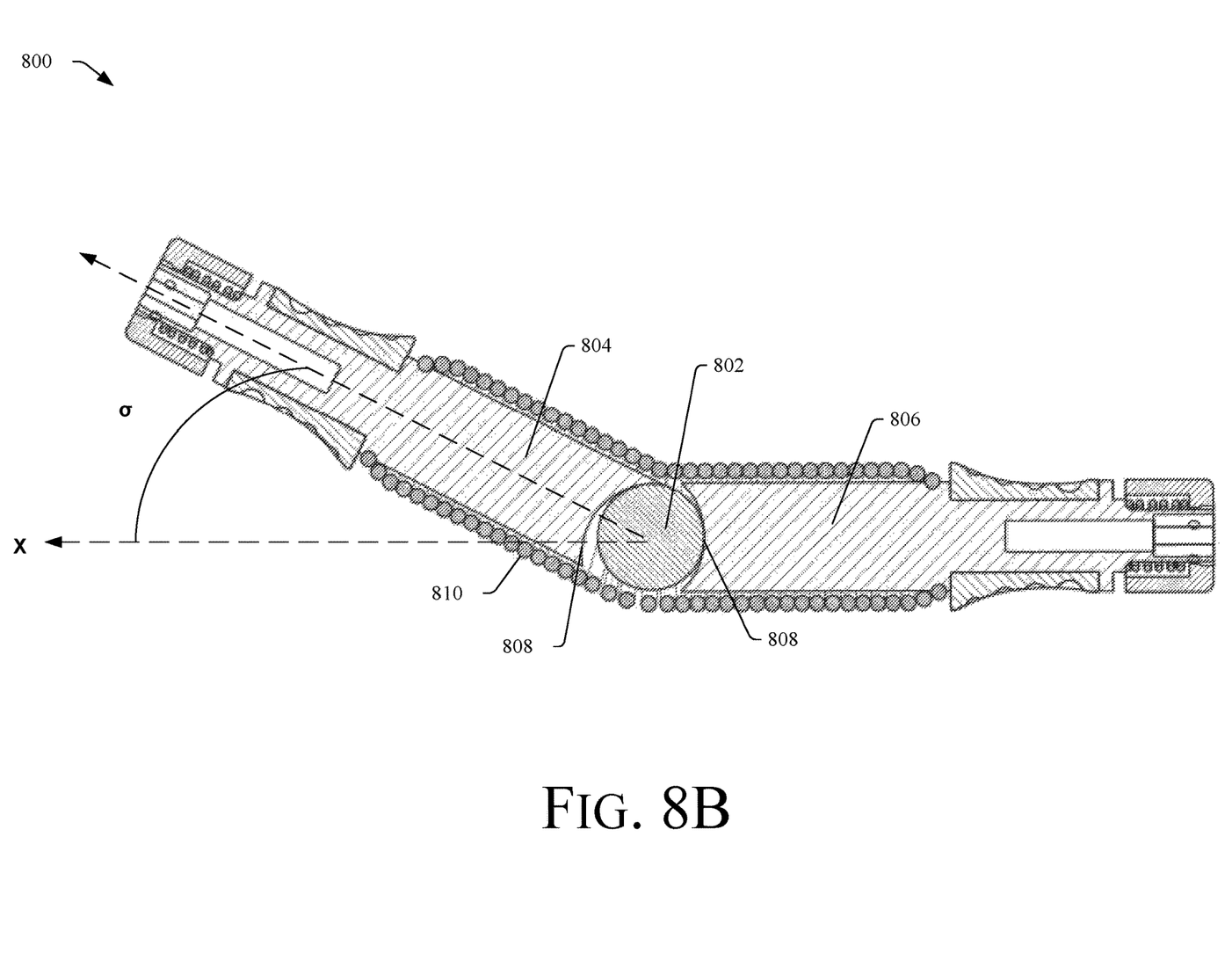
FIG. 8B is a side cross-sectional view of the example spring-driven impact device shown in FIG. 7A deviated at an angle from a horizontal axis of the device.

In various examples, the ball bearings 902(1) and 902(2) may be configured to transfer energy from a moving anvil (e.g., anvils 904 or 906) to a non-moving anvil (e.g., the other anvil 904 or 906). The ball bearings 902(1) and 902(2) may permit a moving anvil to be pulled at an angle (σ) from the X-axis of the spring tool 900, without damaging the spring. In some example, the angle σ may include an angle less than 90 degrees. In some examples, the angle σ may include an angle between 90-120 degrees. In some examples, the two-ball bearing configuration shown in FIG. 8 may permit a greater deviation from the X-axis than the single-ball bearing configuration shown in FIGS. 7A and 7B.

In some examples, the ball bearings 902 may be coupled to a spring 810 of the spring tool 900. In such examples, the ball bearings 902 may be fixed in place in the spring tool 900. In various examples, the ball bearings 902 may be configured to freely move inside the spring 810, responsive to one or both anvils moving. For example, during use of the spring tool, the first anvil 904 may be pulled away from the ball bearing 902(1) and the second anvil 906. Responsive to the first anvil 904 being moved away from the rest position adjacent to the ball bearing 902(1), the ball bearings 902(1) and 902(2) may be free to move (i.e., roll) interior to the spring 810, between the first anvil 904 and the second anvil 906. In various examples, inner portions of the first anvil 904, the second anvil 906, and the ball bearings 902 may be encased in a flex tube. In such examples, the ball bearings 902 may be configured to freely move inside the flex tube. The flex tube may comprise a material configured to flex and stretch, such as a plastic material, an elastic material, or a combination of the foregoing.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. A hand-held spring-driven impact device comprising:
 a helical spring comprising a first end and a second end;
 a first anvil coupled to the first end, the first anvil co p sing:
  a first gripping surface extending along a first portion of an outer surface of the first anvil;
  a chamber at an outer end and extending a first length inward toward an inner end of the first anvil;
  a housing extending a second length inward from the chamber;
 a second anvil coupled to the second end, the second anvil comprising a second gripping surface extending along a second portion of an outer surface of the second anvil;
 a ball bearing housed interior to the helical spring and between the inner surface of the first anvil and an inner surface of the second anvil, wherein the inner surfaces of the first and the second anvil are adjacent to opposite sides of the ball bearing when the helical spring is in a rest position; and
 a locking mechanism coupled to the first anvil, wherein locking mechanism is configured to removeably couple a tip into the chamber.

2. The hand-held spring-driven impact device as claim 1 recites, wherein the locking mechanism comprises a spring-type locking mechanism, the spring-type locking mechanism comprising a ball-shaped lock configured to retract when a spring of the spring-type locking mechanism is compressed and to extend when the spring of the spring-type locking mechanism is released.

3. The hand-held spring-driven impact device as claim 1 recites, wherein the locking mechanism comprises one or more cam paths configured house one or more pins extending outward from the tip.

4. The hand-held spring-driven impact device as claim 3 recites wherein the one or more cam paths include a first portion oriented in along an axis of the hand-held spring-driven impact device and a second portion oriented between 90 degrees and 135 degrees from the axis.

5. The hand-held spring-driven impact device as claim 1 recites, wherein the first anvil is coupled to the spring at the second end by a screw-type coupling.

6. The hand-held spring-driven impact device as claim 1 recites, wherein the chamber comprises at least one of:
 an octagonal shape;
 a hexagonal shape;
 a square shape; or
 a cylindrical shape.

7. The hand-held spring-driven impact device as claim 1 recites, wherein the tip comprises a base portion configured to be secured in the chamber and an end portion, the end portion comprising at least one of:
 a chisel;
 a gouge; or
 an osteotome.

8. The hand-held spring-driven impact device as claim 1 recites, wherein the tip comprises a base portion configured to be secured in the chamber and two end portions, the at least two end portions comprising at least one of:
   a cross-recess head; a blade-type head;
   a hex key;
   a Torx® head;
   a pin punch;
   a letter punch;
   a number punch;
   a shaped punch;
   a single-prong spear; or
   a multi-prong spear.

* * * * *